United States Patent
Hakimuddin (10) Patent No.: US 11,249,065 B2
(45) Date of Patent: Feb. 15, 2022

(54) TESTING PETRO-PHYSICAL PROPERTIES USING A TRI-AXIAL PRESSURE CENTRIFUGE APPARATUS

(71) Applicant: Saudi Arabian Oil Company, Dhahran (SA)

(72) Inventor: Mustafa Hakimuddin, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 236 days.

(21) Appl. No.: 16/393,059

(22) Filed: Apr. 24, 2019

(65) Prior Publication Data

US 2020/0340973 A1 Oct. 29, 2020

(51) Int. Cl.
G01N 11/00 (2006.01)
G01N 33/38 (2006.01)

(52) U.S. Cl.
CPC ........... *G01N 33/383* (2013.01); *G01N 11/00* (2013.01)

(58) Field of Classification Search
CPC .............................. G01N 33/383; G01N 11/00
USPC ............................................................. 73/37
See application file for complete search history.

(56) References Cited

U.S. PATENT DOCUMENTS

| | | |
|---|---|---|
| 4,555,934 A | 12/1985 | Freeman et al. |
| 4,671,102 A | 6/1987 | Vinegar et al. |
| 5,159,828 A | 11/1992 | Steiger |
| 5,253,529 A | 10/1993 | Lenormand et al. |
| 5,265,461 A | 11/1993 | Steiger |
| 5,275,063 A | 1/1994 | Steiger |
| 5,325,723 A | 7/1994 | Meadows et al. |
| 5,493,226 A | 2/1996 | Honarpour et al. |
| 5,563,333 A | 10/1996 | Haines et al. |
| 5,568,262 A | 10/1996 | LaChapelle |
| 6,178,807 B1 | 1/2001 | Baldwin et al. |
| 6,833,699 B2 | 12/2004 | Galford et al. |
| 6,935,159 B2 | 8/2005 | Knight et al. |

(Continued)

FOREIGN PATENT DOCUMENTS

| | | |
|---|---|---|
| CN | 106053231 | 10/2016 |
| SU | 1508147 | 9/1989 |
| WO | WO 2004074762 | 9/2004 |

OTHER PUBLICATIONS

Tiab et al., Petrophysics, Theory and Practice of Measuring Reservoir Rock and Fluid Transport Properties, 2nd ed., Elsevier, 2004, 927 pages.

(Continued)

*Primary Examiner* — John Fitzgerald
*Assistant Examiner* — Rodney T Frank
(74) *Attorney, Agent, or Firm* — Fish & Richardson P.C.

(57) ABSTRACT

A system for testing properties of a sample, the system including a test cell. The test cell includes a cell casing having a first end piece, a second end piece, and at least one wall extending between the first end piece and the second end piece. The cell casing defines a pressure boundary enclosing an interior region of the cell. The test cell further includes a sample chamber, a first reservoir, and a second reservoir disposed within the pressure boundary. The sample chamber defines an interior region. The first reservoir fluidly connects to the interior region of the sample chamber. The second reservoir fluidly connects to the interior region of the sample chamber. The test cell also has a piston assembly having a piston fluid chamber and a piston with a stem extending into the piston fluid chamber. The piston partially defines the sample chamber.

13 Claims, 8 Drawing Sheets

(56) References Cited

U.S. PATENT DOCUMENTS

| | | |
|---|---|---|
| 6,971,260 B2 | 12/2005 | Potter |
| 7,055,374 B2 | 6/2006 | Abdel-Hadi |
| 7,092,822 B2 | 8/2006 | Lenormand et al. |
| 7,352,179 B2 | 4/2008 | Chen et al. |
| 7,412,875 B2 | 8/2008 | Zomberg et al. |
| 7,712,526 B2 | 5/2010 | Morgan et al. |
| 8,024,960 B2 | 9/2011 | Fleury et al. |
| 8,224,629 B2 | 7/2012 | Green |
| 8,443,661 B1 | 5/2013 | Bi |
| 8,794,078 B2 | 8/2014 | Darbe et al. |
| 8,805,616 B2 | 8/2014 | Hinkel et al. |
| 8,894,559 B2 | 11/2014 | Alomair |
| 2005/0103094 A1 | 5/2005 | Knight |
| 2005/0150273 A1 | 7/2005 | Potter |
| 2010/0200242 A1 | 8/2010 | Rodger et al. |
| 2010/0274367 A1 | 10/2010 | Kaufman |
| 2010/0313645 A1 | 12/2010 | Doman et al. |
| 2011/0050223 A1 | 3/2011 | Balcom et al. |
| 2012/0151998 A1 | 6/2012 | Willberg et al. |
| 2012/0304763 A1 | 12/2012 | Troxler |
| 2015/0111716 A1 | 4/2015 | Hakimuddin |
| 2017/0074093 A1 | 3/2017 | Adebayo et al. |
| 2018/0353954 A1 | 12/2018 | Pennie |
| 2019/0087939 A1 | 3/2019 | Hakinuddin |

OTHER PUBLICATIONS

PCT International Search Report and Written Opinion in International Appln. No. PCT/US2020/029460, dated Jul. 28, 2020, 17 pages.

Chryssanthakis et al., "High temperature triaxial tests with ultrasonic on Ekofisk chalk," 37th U.S. Symposium on Rock Mechanics (USRMS), Rock Mechanics for IndusUy, Jun. 7-9, 1999, pp. 373-379, 8 pages.

International Search Report and Written Opinion issued in International Application No. PCT/US2014-061313 dated Feb. 25, 2015, 9 pages.

Josh et al., "Laboratory characterization of shale properties," Journal of Petroleum Science and Engineering, Jun. 2012, 18 pages.

Kuila et al., "Stress ansiotrophy and velocity ansiotrophy in low porosity shale," Tectonophysics, 2011, vol. 503, Issue 1-2, Apr. 2011, 11 pages.

Meissner et al., "State of the Art Special Core Analysis Program Design and Results for Effective Reservoir management," International Petroleum Technology Conference, Doha, Qatar, 2009, 1 pg (Abstract).

O'Meara Jr. et al., "Centrifuge Measurements of Capillary Pressure: Part 1—Outflow Boundrary Condition," Society of Petroleum Engineers, SPE, Feb. 1992, 1 pg, (Abstract).

Onitsuka et al., "A study on the relationship between mechanical properties and microstructure of Ariaka Clay," ISOPE, International Society of Offshore and Polar Engineers, Ninth international Offshore and Polar Engineering Conference, May 30-Jun. 4, 1999 (Abstract).

Sarout et al., "Shale dynamic properties and anisotrophy under triaxial loading: Experimental and theoretical investigations," Physics and Chemistry of the Earth, Parts A/B/C, vol. 32, Issue 8-14, 2007, 11 pages.

Straley et al., "NMR in partially saturated rocks: Laboratory insights on free fluid index and comparison with borehole logs," SPWLA Jun. 16-19, 1991, 25 pages.

Unalmiser et al., "Engineering Core Analysis," Distinguished Author Series, Apr. 1998, SPE 36780, 7 pages.

Wang et al., "Simultaneous core sample measurements of elastic properties and resistivity at reservoir condutions employing a modified triaxial cell—a feasibility study," Geophysical Prospecting, Oct. 8, 2009, pp. 1009-1026, vol. 57, EAGE, 19 pages.

Yao et al., "Petrophysical characterization of coals by low-field nuclear magnetic resonance (NMR)," Fuel 2010, vol. 89, Jul. 2010, 10 pages.

PCT International Search Report and Written Opinion in International Application No. PCT/US2020/029,607, dated Nov. 9, 2020, 18 pages.

Bin-Quan, "Rock Petrophysics Experiment in Medium-deep Gas Reservoirs," Chinese Maters Thesis Full-Text Database Basic Sciences, pp. A011-41, vol. 3, Apr. 2007, abstract only, 98 pages.

PCT Invitation To Pay Additonal Fees and Where Applicable, Protest Fee in International Application. No. PCT/US2020/029,607, dated Sep. 17, 2020, 11 pages.

TESTING PETRO-PHYSICAL PROPERTIES USING A TRI-AXIAL PRESSURE CENTRIFUGE APPARATUS

TECHNICAL FIELD

This invention relates to systems and methods for testing petro-physical properties using a tri-axial pressure centrifuge system.

BACKGROUND

Tri-axial tests can be used to measure the mechanical properties of subterranean formations. For example, in tri-axial shear tests, stress is applied to a sample from the subterranean formation with stresses along one axis being different from the stresses in perpendicular directions. The application of different compressive stresses in the test apparatus causes shear stress to develop in the sample with loads being increased and deflections monitored until failure of the sample. Pore pressures of fluids (for example, water, or oil) and other properties in the sample may be measured during the testing.

SUMMARY

The system and methods described in this specification are able to perform a variety of tests on one single system to measure and sense petrophysical, fluid phase behavior, formation damage, and enhance oil recovery data needed for estimating reservoir capacity and recovery of hydrocarbons. The systems can measure electrical properties to calibrate electrical log, fluid saturation, and Archie's parameter, apply capillary pressure above 1000 pounds per square inch (psi), to perform fluid wettability test, measure acoustic velocity for dynamic mechanical properties, perform x-ray for saturation distribution, perform reservoir fluid compressibility, and determine change in fluid properties (static, dynamic, physical, and compositional). The same systems are able to do perform these measurements and tests while applying tri-axial conditions that are observed in the field.

Some systems for testing properties of a sample include: a test cell including: a cell casing comprising a first end piece, a second end piece, and a cylindrical body extending between the first end piece and the second end piece, the cell casing enclosing an interior region of the cell; a piston with a stem and a head, the head of the piston in sealing engagement with an inner surface of the cylindrical body of the test cell wherein the piston head and the first end piece at least partially define a sample chamber; an inner channel extending through the stem of the piston that extends to the sample chamber; and a conduit attached to the inner channel that extends from the stem of the piston through the second end piece. Embodiments of these systems can include one or more of the following features.

In some embodiments, the piston is part of a piston assembly, the piston assembly also comprising a piston fluid chamber defined in the second end piece. In some cases, the conduit extends through the piston fluid chamber.

In some embodiments, the sample chamber is defined by the piston head, the first end piece, and the cylindrical body of the test cell. In some cases, the systems include 5. The system of claim 4, further comprising a pore fluid channel defined by the first end piece, the pore fluid channel extending from the sample chamber through the cell casing.

In some embodiments, the sample chamber is defined by the piston head, the first end piece, and a cylindrical jacket parallel to the cylindrical body of the test cell, the cylindrical jacket extending between the piston head and the first end piece. In some cases, the systems include an overburden fluid supply line extending from a portion of the interior region outside the sample chamber through the cell casing.

In some embodiments, a surface of the first end piece exposed to the sample chamber is flat.

In some embodiments, systems include one or more processing units implementing a neural network. In some cases, the systems include an electrical probe incorporated in the first end piece adjacent the sample chamber, the electrical probe in communication with the neural network. In some cases, the systems include a first acoustic sensor incorporated in the second end piece, the first acoustic sensor in communication with the neural network. In some cases, the systems include a second acoustic sensor incorporated in the first end piece, the second acoustic sensor in communication with the neural network.

Some methods for testing a sample in a centrifuge apparatus include: bringing a test cell to test pressure and test temperature with a piston head of the test cell in contact with an end piece of the test cell; introducing a fluid sample being tested between the piston head and the end piece of the test cell; equilibrating the fluid sample; performing at least one speed test on the fluid sample; and feeding acoustic, electrical, and x-ray data gathered from sensors associated with the test cell or the centrifuge apparatus to a neural network. Embodiments of these methods can include one or more of the following features.

In some embodiments, the methods include using the neural network to evaluate whether the sample is acceptable. In some cases, methods include discarding the sample if it is unacceptable. In some cases, a neural network is used to determine if the sample is unacceptable.

In some embodiments, bringing the test cell to test pressure comprises injecting an inert fluid into the test cell.

In some embodiments, the methods include changing test parameters and performing at least one speed test on the sample under the changed test parameters. In some cases, changing test parameters comprises at least one of changing test pressure, changing test temperature, withdrawing a fluid sample and perform compositional analysis, and modifying the test fluid.

In some embodiments, the methods include lowering system temperature to ambient conditions while keeping system pressure constant. In some cases, methods include lowering system pressure to ambient conditions.

In some embodiments, the methods include filling the test cell with an overburden fluid with the piston head of the test cell in contact with the end piece of the test cell before bringing the test cell to test pressure and test temperature. In some cases, introducing the fluid sample being tested between the piston head and the end piece of the test cell comprises introducing a cement sample between the piston head and the end piece of the test cell. In some cases, methods include injecting water to a space between the piston head and the end piece of the test cell. In some cases, methods include setting and curing the cement sample. In some cases, methods include measuring and removing free water after the cement sample is set and cured. In some cases, methods include performing at least one test on the sample. In some cases, methods include changing test parameters and performing at least one test on the sample under the changed test parameters.

Further, the system can perform formation damage studies on reservoir rock under tri-axial reservoir conditions, with reservoir pore pressure, and can exert controlled capillary pressure. This system can also contain material that is corrosive and/or reactive to formation rocks and fluids.

Some of these systems and methods can be used to perform cement tests to evaluate property of cements used in reservoir. Properties may be, for example, thickening time, free water, bonding, setting time, sonic velocity, electrical properties, and mechanical strength. These tests can be performed under reservoir temperature, pressure, and pore pressure in presence of reservoir fluids and reservoir rock. The instrument can also measure flow properties of cement at various stages of cement life cycle under tri-axial and pore pressure conditions.

Some of these systems and methods can be used to study formation, dissociation and production of gas hydrates under tri-axial and pore pressure conditions with reservoir materials (sand, rock, fluids), as well as investigate flow properties of the reservoir material under capillary pressure conditions.

Some of these systems and methods can be used to evaluate petrophysical properties of unconventional reservoir (tight gas sand, shale, source rock etc.) under tri-axial and pore pressure condition encountered in reservoir, under capillary pressure stress regime. Additionally, the system may provide the capability to simulate fracturing and propant injection tests required for production of unconventional tight reservoirs.

The details of one or more embodiments of these systems and methods are set forth in the accompanying drawings and the description below. Other features, objects, and advantages of these systems and methods will be apparent from the description and drawings, and from the claims.

DESCRIPTION OF DRAWINGS

Like reference symbols in the various drawings indicate like elements.

DETAILED DESCRIPTION

This specification describes systems and methods that can recreate reservoir conditions on geological samples. These systems and methods can be used to generate reservoir temperatures, reservoir confining pressures, reservoir axial stresses, and reservoir pore pressures under capillary pressures encountered during reservoir exploitation. These systems and methods can also be used to collect flow, pressure, temperature, x-ray, sonic, electrical, and dimensional properties of a sample. A variety of tests can be performed by these systems including, for example, single-speed flow tests, multi-speed flow tests, single-speed capillary tests, multi-speed capillary tests, electrical property tests, acoustic velocity tests, cement bond tests, and gas leakage tests. These systems and methods can also be used to analyze generated data by utilizing artificial intelligence techniques during the tests.

Figure 1:
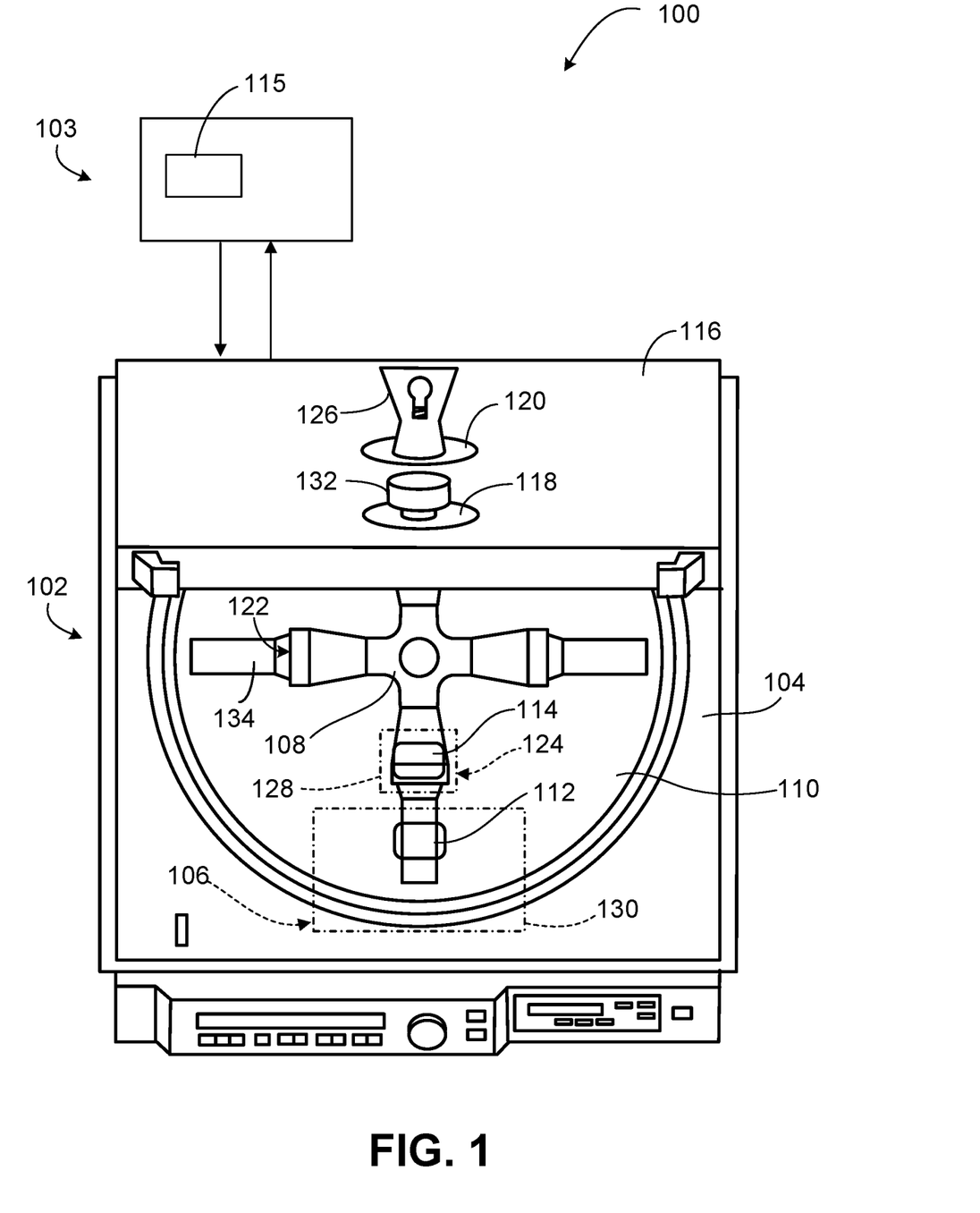
FIG. 1 is a schematic perspective view of a system for triaxial testing of a sample using a centrifuge.

FIG. 1 shows a system 100 for testing petro-physical properties and gathering geo-mechanical information of a sample arranged within the system 100. The system 100 includes a centrifuge apparatus 102 and a computer system 103. The centrifuge apparatus 102 includes a centrifuge 104 and an x-ray device 106. The centrifuge apparatus 102 has a rotor 108 and a tub 110. This configuration can provide a high capillary pressure by spinning samples at given revolutions per minute (rpm). The tub 110 of the centrifuge apparatus 102 has a first tub window 112 and a second tub window 114. A lid 116 of the centrifuge apparatus 102 has two lid windows 118, 120 aligned with the tub windows 112, 114 for x-ray scanning and visual scanning.

The computer system 103 is in communication with components of the centrifuge apparatus 102. The computer system 103 can be used to control operation of the centrifuge apparatus and receive, process, and store data generated by the centrifuge apparatus 102. In the system 100, the computer system 103 is used to implement a neural network 115 that assesses and processes tests being performed using the centrifuge system. An example of an implementation of a neural network is described in detail in U.S. patent application Ser. No. 16/131,341 ("Inferring Petrophysical Properties of Hydrocarbon Reservoirs Using a Neural Network") filed on Sep. 14, 2018. In the system 100, the computer system 103 is separate from the centrifuge apparatus 102. In some systems, the computer system 103 is incorporated into the centrifuge apparatus 102.

The system 100 has four recesses 122 that are each sized to receive a test cell. In the system 100, the recesses 122 are in the rotor 108 of the centrifuge apparatus 102. In some embodiments, the centrifuge apparatus may have more than four recesses or less than four recesses. The number of tri-axial cells placed in the centrifuge apparatus 102 is based on specific test parameters. In some embodiments, the centrifuge apparatus 102 is a Roto-Salina centrifuge commercially available from Hettich, which is configured to provide more than 20,000 rpm.

Visual scanning is executed by a fluid camera system 124 that includes a visual camera light source 126 and a visual camera 128. The visual camera light source 126 can be a strobe light and the visual camera 128 can be a high-speed camera to capture images as the test progress. The fluid camera system 124 is designed to work both in transmission and reflection mode. The visual camera light source 126 and visual camera 128 can be installed on the opposite side of the test sample (for example, top and bottom) or on the same side (for example, top) and use a reflective mirror setup in the tub 110 to capture images. The mirror setup can be utilized in cases of limited access on the tub. In the system 100, the visual camera light source 126 is installed above the lid 116 of the centrifuge apparatus 102 and visual camera 128 is installed below the tub 110. Use of such a fluid camera system 124 allows for reading of fluid volumes as they are produced.

The x-ray device 106 includes an x-ray source 130 and an x-ray camera 132. The x-ray device 106 images a test cell 134 received by the recess 122 in the rotor 108. The x-ray camera 132 is arranged on the lid 116 of the centrifuge apparatus 102 over the first lid window 118.

The data collected can include, for example, acoustic, temperature, electrical, x-ray, saturation, fluid volumes, rate of fluid volumes, and saturation change. The resulting comprehensive picture of test progression can be integrated with well log and seismic data for monitoring and evaluating effectiveness of field treatment. Temperature can be monitored using temperature sensors and saturation changes can be monitored with the x-ray device 106. Electrical data can be generated for wells where well-logs are not available or are not representative with a combination of seismic, acoustic, electrical and saturation data, along with well test information.

Centrifuge capillary pressure tests under tri-axial, confined, and unconfined stress conditions can be performed with the centrifuge apparatus 102. In some embodiments, capillary pressure over 20,000 pounds per square inch (psi) for an oil/gas/water system can be applied. The range of capillary pressures to be tested will depend on the type of reservoir. For example, capillary pressures can range from 0.1 psi to 100 psi for unconsolidated sand reservoirs; 1 psi to 134 psi for conventional reservoirs; and 100-100,000 psi for unconventional reservoirs like shale and tight gas sand (TGS). It should be noted that in instances with a capillary pressure of above 30,000 psi, sample integrity can be an issue. In many such cases, a work-around can be developed by increasing the tri-axial stress. The test can be conducted as air/water, air/oil, water/oil, and, in limited cases, all three phases (air/oil/water) on the rock sample. Some systems allow for extracting fluids from reservoir core samples at a capillary pressure of 20,000 psi and higher. In some embodiments, capillary pressure above 20,000 psi is achieved by increasing motor speed, by increasing the size of tub 110, by increasing the distance between the test sample and center of centrifuge apparatus 102, and/or by changing sample size and orientation. In some embodiments, the test sample is loaded in the centrifuge apparatus 102 in a vertical orientation. In other embodiments, the test sample is loaded in the centrifuge apparatus 102 in a horizontal orientation. Some test samples are about 0.5 inches to about 8 inches in diameter and about 0.5 inches to about 12 inches in length.

Figure 2:
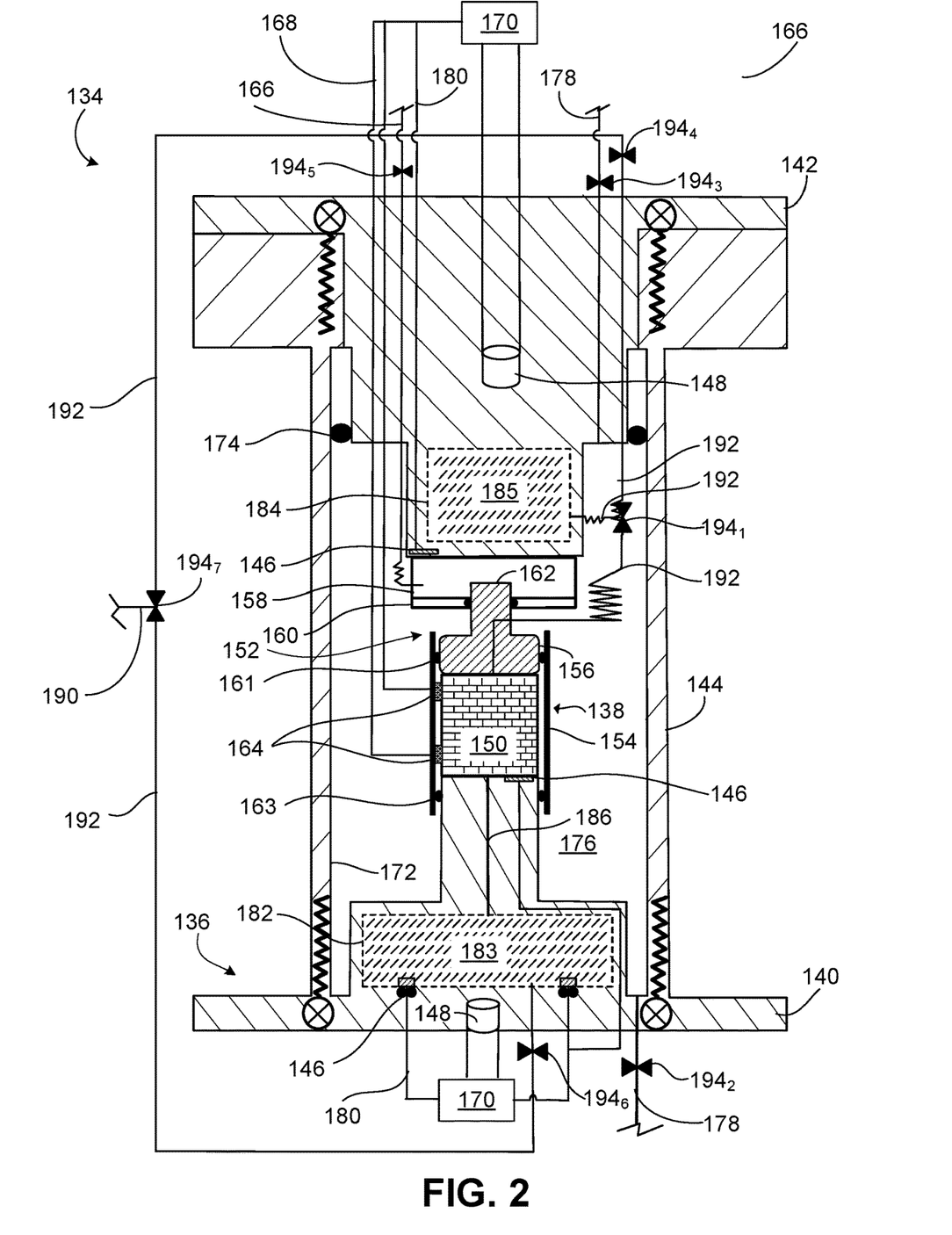
FIG. 2 is a schematic cross-sectional view of a test cell.

FIG. 2 shows a test cell 134 with a casing 136 containing a sample holder 138. The casing 136 includes first end piece (a base 140), a second end piece (an end cap 142), a body 144 extending between the base 140 and the end cap 142, at least one electrical sensor 146, and at least one acoustic sensor 148.

The sample holder 138 is configured to hold test samples 150 such as solid cores from a reservoir. The sample holder 138 includes a piston assembly 152 and a jacket (for example, electrical measurement jacket 154) extending between the piston assembly 152 and the base 140 of the casing 136. In general, materials for the piston assembly 152 and the portion of base 140 adjacent the sample should be penetrable to x-rays and have minimal or no electrical conductance and can be, for example, Torlon® (available from Solvay Plastics) or glass. Piston assembly 152 includes a piston member 156, and a piston fluid chamber 158. An axial pressure fluid supply line 166 supplies fluid to piston fluid chamber 158. A fluid chamber base 160 has an opening through which the stem 162 of piston member 156 extends. An end face of piston member 156 engages a first end of sample 150.

Base 140 has an end face that engages a second end of sample 150 that is opposite the first end of sample 150. Sample 150 is contained between the end face of the piston member 156 and the end face of base 140. As fluid is added to the piston fluid chamber 158 by way of axial pressure fluid supply line 166, the end face of piston member 156 applies axial force on the first end of sample 150, inducing axial stress in sample 150. The end face of piston assembly 152 and the end face of the base 140 can be coated with a substance, such as Teflon®, that will provide electrical isolation of the sample 150.

In some embodiments, the sample holder 138 includes the electrical measurement jacket 154. The electrical measurement jacket 154 is a non-permeable, elastomeric, rubber or polyurethane jacket and can be made, for example, of Viton® (available from DuPont). Electrical measurement jacket 154 is a tubular member that surrounds the sample 150. A piston seal 161 forms a seal between the inner bore of a first end of electrical measurement jacket 154 and an outer surface of piston member 156. A base seal 163 forms a seal between the inner bore of a second end of the electrical measurement jacket 154 and an outer surface of base 140.

The electrical measurement jacket 154 is equipped with jacket sensors 164 to provide additional measurements of electrical properties of the test sample and saturation distribution data. The electrical measurement jacket 154 is made by incorporating the jacket sensors 164 during a vulcanization process of jacket making The type of jacket sensors 164, number of sensors, and their location is based on sample size and sample property, such as its mineral composition and homogeneity. The number of jacket sensors 164 in the electrical measurement jacket 154 can be increased and distributed such that various electrical measurements are performed on the sample 150 and the collected electrical measurement values can provide an electrical image. The data collected by the jacket sensors 164 can be transmitted by way of leads 168 to a processing unit 170. This type of data gathering can be extremely valuable for heterogeneous samples with layering, unconnected pore structure, fracture, kerogen concentration, and other sample anomalies. The data from multiple jacket sensors 164 can be used measure electrical resistance across the sample 150 and to produce an image of rock lithology and geology.

In some embodiments, the system 100 includes electrical measurement feeds 180 associated with the base 140. The base 140 is designed with material that is electrically insulated and is embedded with electrodes (electrical sensors 146) for performing 2 or 4 electrode conductivity and resistivity measurements. The electrical measurement feeds 180 are connected to electrodes (electrical sensors 146) of the base 140 to deliver signals to a processing unit 170 for data collection regarding reservoir salinity information from native state samples which will allow for better reserve estimation. In certain embodiments, the electrical measurement feeds 180 can provide current and measure the voltage with a small battery operated device (not shown) that can be installed on the rotor 108 of centrifuge apparatus 102 (FIG. 1) and connected to the test cell 134.

A variety of electrical measurements can be taken during testing. For instance, in some embodiments electrical analysis of the sample 150 includes measuring at least one of the resistance, conductivity, capacitance, or impedance of the test sample. In some embodiments, electrical analysis of the sample 150 includes measuring at least one of electrical conductance, resistance, or impedance as a function of variable frequency of input current. In some embodiments, the end cap 142 of the casing 136 is designed such that it is isolated from the rest of the casing 136 and acts as an electrode. The body 144 of the casing 136 can be used as a ground to measure the electrical properties of the sample 150 during a test. Electrical measurements can be taken various ways during a test. In one approach, the centrifuge apparatus 102 is stopped at each capillary pressure equilibrium step, the test cell 134 is taken out of the centrifuge apparatus 102, and the electrical properties of the sample in the test cell 134 are measured. Depending on the test design, additional equilibrium steps can be required. In some embodiments, there can be 2 to 15 equilibrium steps and measurements can be performed at each step. In another approach, processing unit 170 includes a battery operated electrical measurement device with capability to gather the time domain data that can be down loaded at the end of test. The advantage of the second method is that it provides a continuous measurement without a need to stop centrifuge apparatus 102 and also provides transit data between the capillary pressure equilibrium stages. The system 100 includes another processing unit 170 that is operable to gather data during the testing of a sample and store data for downloading at a later time. In some embodiments, the data is downloaded in real time. The electrical data collected on the sample 150 can be collected simultaneously as the other data is collected, or in sequential steps to the other data. In some embodiments, an electrical sensor 146 measures the electrical properties of fluid contacting the surface of the casing 136.

The test cell 134 is illustrated with multiple processing units 170. In system 100, the computer system 103 and the associated neural network 115 are in communication with two processing units 170 in the test cell 134. Some test cells have a single processing unit. The processing unit(s) can be incorporated in or external to the test cell 134. For example, in some systems, the computer system 103 and the associated neural network 115 provide the functionality of the processing units 170 and are in direct communication the sensors and valves of the test cell.

As previously discussed, the casing 136 includes the base 140, the end cap 142, and the body 144 extending between the base 140 and the end cap 142. The body 144 is a generally cylindrical member with an inner bore 172. The base 140 and the end cap 142 are bolted to the body 144 of the casing 136. A casing seal 174 limits the flow of fluid between the inner surface of inner bore 172 and the outer surface of the reduced diameter portion of end cap 142.

When assembled, the base 140, the end cap 142, and the body 144 define a cell chamber 176. Confining pressure fluid supply lines 178 delivers fluid to cell chamber 176 for applying biaxial stress on the sample 150.

In some embodiments, the casing 136 is made of titanium. Titanium allows for x-ray scanning while the test is in progress. In other embodiments, the casing 136 is made of Torlon® or glass. In general, materials for the test cell 134 should be penetrable to x-rays and have minimal or no electrical conductance. In further embodiments, the casing 136 and sample holder 138 include both internal and external coatings that are resistant to acids and corrosive chemicals, such as hydrochloric acid, acetic acid, or other acids that would be used to mimic well cleaning and stimulation tests, as well as acids that would be used for chemical enhanced oil recovery (EOR). The test cell 134 is capable of performing centrifuge saturation and capillary pressure test at unconfined, confined, hydrostatic, or tri-axial test conditions.

The acoustic sensors 148 can each be an acoustic sensor with p-wave and s-wave components. Acoustic sensor 148 can be a dual mode transducer capable of both sending and receiving information. In some embodiments, the acoustic sensor 148 is located on or in the end cap 142. In some embodiments, the end cap 142 is isolated from the body 144 of the sample holder 138 such that electrical properties can be measured using electrical sensors 146 in the end cap 142 and the body 144 of the sample holder 138 as ground. In such an embodiment, electrical sensors 146 of end cap 142 can provide electrical information by way of leads to a processing unit 170.

The acoustic sensor 148 in the base 140 provides two functions. It provides a thru transmission between the test specimen and the two fluid chamber to provide an overall quality assessment when in transmission mode. In reflection mode, both the top and bottom acoustic sensors provide specific changes within each fluid reservoir providing an indication of the separation of various fluids within the fluid chamber. The pore pressure fluids are sensitive to pressure on them, as solid or gas can be produced due to pressure variations and may cause various fluid layers within the fluid chambers. The acoustic sensors will aid in understanding fluid behavior in each chamber that may not be clearly observable using only an x-ray scan of the fluid chambers. This functionality is important in system which apply pore pressure but not relevant to systems which do not apply pore pressure to the sample. When there is no pore pressure, there are no fluid properties variations as function of fluid pressure, so a bottom acoustic sensor is not required.

A variety of acoustic measurements can be taken during testing, including sonic velocity data. In some embodiments, the acoustic sensor 148 can collect longitudinal wave, shear wave, and/or Stonely wave data. The acoustic data collected can be delivered to processing unit 170 by way of leads and analyzed for both time and frequency domain. The same acoustic sensor can collect the various wave forms, as one transducer can encompass crystals for longitudinal and shear wave. In preferred embodiments, the acoustic sensor 148 is a transducer with both longitudinal wave and shear wave components which are installed on the end cap 142 of the casing 136. In some embodiments, the acoustic sensor 148 is a dual mode transducer and works in reflective mode to transmit and receive acoustic wave. In some embodiments, the system 100 is operable to measure the acoustic velocity of the sample 150, as well as the velocities of the various fluids in the base 140. The same acoustic sensor can perform all of the desired the measurements with proper calibration of the acoustic sensor 148 before the test starts and once the test is concluded, dependent on rock sample properties and fluid used during the test. The acoustic velocity of the fluid in the base 140 can be used to analyze production and presence of solid particles such as grain, asphaltene, and so forth. In general, special care should be taken to assure that the acoustic sensor 148 and associated components does not interfere with electrical measurements. The acoustic data collected on the sample 150 can be collected simultaneously with the other data, or in sequential steps to the other data.

The base 140 of the casing 136 includes a first reservoir 182 defined in the base 140. The end cap 142 of the casing 136 includes a second reservoir 184 defined in the end cap 142. Depending on the test type, the first reservoir 182 and the second reservoir 184 can hold fluids such as, for example, fluid samples from the sample 150, or fluids to be injected into the sample 150 such as solvents, acids, or chemicals for EOR. The walls of the first reservoir 182 and the second reservoir 184 have neutral wettability. Neutral wettability helps separate air, water, and hydrocarbon fluids quickly and with a sharp contrast. In some tests, the first reservoir 182 contains a first fluid 183 and the second reservoir 184 holds a second fluid 185. The fluids can have different densities. For example, the first fluid 183 can be denser than the second fluid 185 to counter the effect of density variation in the two fluids and to mimic the gravity variation during the loading of test specimen.

As previously discussed, the base 140 and the end cap 142 are made of materials that provide a low x-ray interference. This design limits interference when the x-ray device 106 images fluids within the first reservoir 182 and second reservoir 184.

A sample line 186 provides fluid communication between sample holder 138 and the first reservoir 182. A pore fluid circulation system 188 also connects the first reservoir 182 and the second reservoir 184 with the sample holder 138. The pore fluid circulation system 188 includes an access line 190 and multiple circulation lines 192 connected and controlled by multiple valves 194. The pore fluid circulation system 188 and the configuration of the reservoirs allows different pressures to be applied to the first reservoir 182, the second reservoir 184, and to the cell chamber 176. In effect, the casing 136 is a first pressure boundary. The first reservoir 182 and the second reservoir 184 are second and third pressure boundaries respectively located within the first pressure boundary. In the test cell 134, the first reservoir 182 is arranged near the base 140 of the casing 136 and the second reservoir 184 is arranged near the end cap 142 of the casing 136. Placing the reservoirs and the sample 150 inside the casing 136 allows tri-axial pressure applied within the test cell 134 to be applied to the first reservoir 182, the second reservoir 184, and the sample 150. The second and third pressure boundaries allow the pore pressure to be controlled independently of the overburden pressure. The application of independent pore pressure, overburden pressure, and tri-axial pressure by the centrifuge apparatus 102 allows the system to more accurately simulate reservoir conditions than systems that lack this functionality. The pressures within the first reservoir 182 and the second reservoir 184 are independently controllable and are kept below the tri-axial pressure being applied by fluid in the cell chamber 176.

The test cell 134 can used to perform the experimental studies including: production mechanism between various pore sizes (macro/micro/nano); understanding imbibition/drainage base production between macro-micro pores; two and three phase relative permeabilities; two and three phase capillary pressure; chemical flooding EOR; wettability alteration study and effectiveness of wettability altering material; acidizing flow test and effectiveness as function of capillary pressure and injection sweep efficiency; residual oil production and sweep efficiency of water alternating gas (WAG) under capillary pressure versus flow; mechanical properties tests for Young Modulus, Poison Ratio and Failure envelope; hydrate formation, dissociation and production (flow) mechanism as function of temperature and/or pressure and/or composition; coal bed methane studies from intact test specimen to fail within the same setup to get residual gas; formation damage studies related to damages due to injected fluids, produced fluids, filtrates, stress change and temperature changes; enhance oil flooding with miscible fluids, non-miscible floods, fluids reactive to reservoir fluids, fluids reactive to reservoir rock and any combination of them; propant strength, propant injection and embedment within reservoir; propant interaction with reservoir fluids and reservoir fluid effects on propant integrity; propant fracture aperture hold capacity and its change as function of stress & fluid composition; propant flow back characteristic, fracture closing and related effect on reservoir production; unconventional shale, tight gas sand and Tar-sand studies; fine migration due to production, stress changes, and fluid compositional changes; condensate flow test as function of composition and pressure drop; condensate wettability and wettability alteration study; low resistivity pay test for understanding formation brine salinity and their effects as function of pore fluids in macro, micro, and nano pores.

Figure 3:
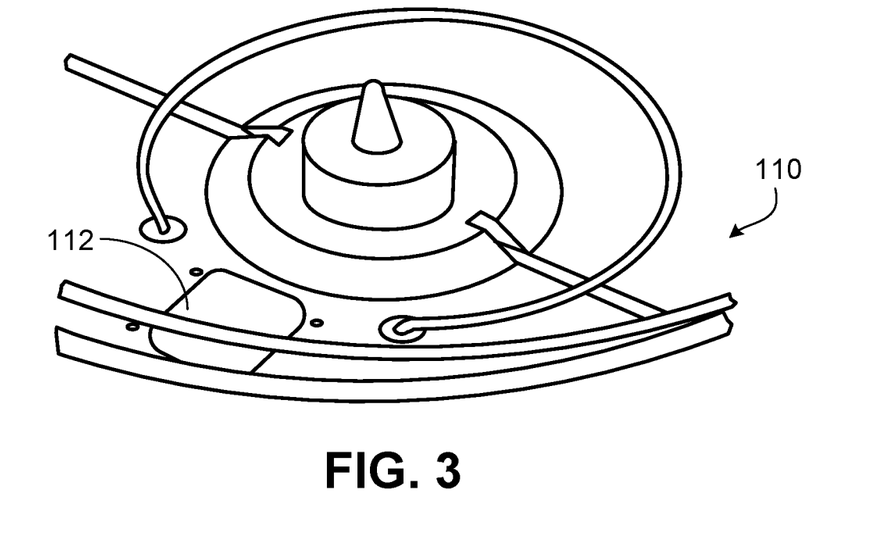
FIG. 3 is a schematic bottom view of a portion of the centrifuge apparatus of FIG. 1.

FIG. 3 is a perspective view of the tub 110 with the tub window 112. In some embodiments, the tub window 112 is made of a transparent material, for example, glass. The tub window 112 is arranged on the tub 110 to align with the x-ray source 130, shown in FIG. 1.

Figure 4:
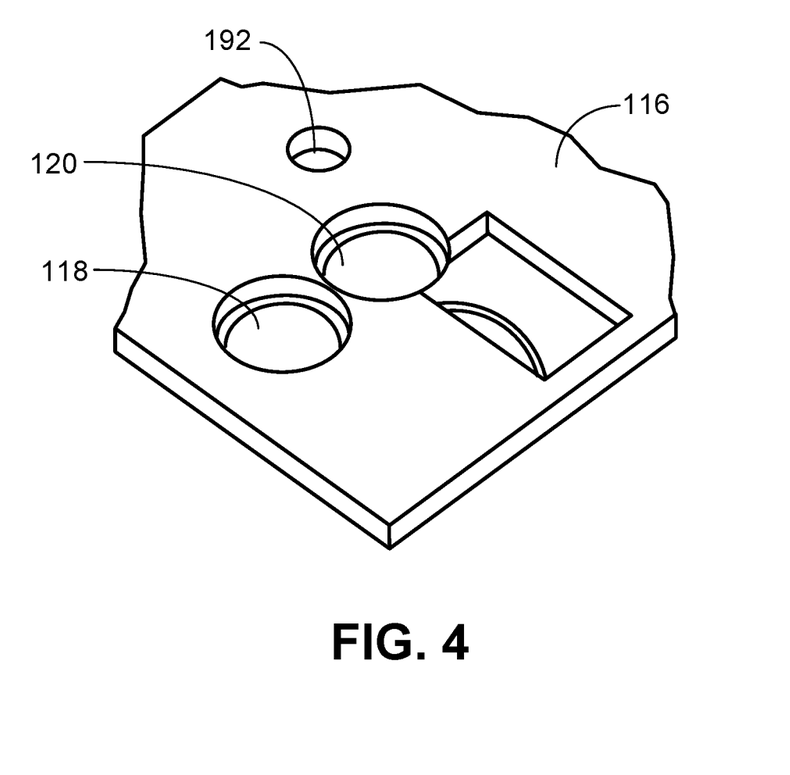
FIG. 4 is a schematic view of a lid of the centrifuge apparatus of FIG. 1.

FIG. 4 is a perspective view the lid 116 having the first lid window 118 and the second lid window 120. The first lid window 118 is opposite the tub window 112 and aligned with the x-ray device 106 shown in FIG. 1. The second lid window 120 is arranged to align with the visual camera light source 126 shown in FIG. 1. A third lid window is arranged to align with the visual camera 128 shown in FIG. 1.

Figure 5:
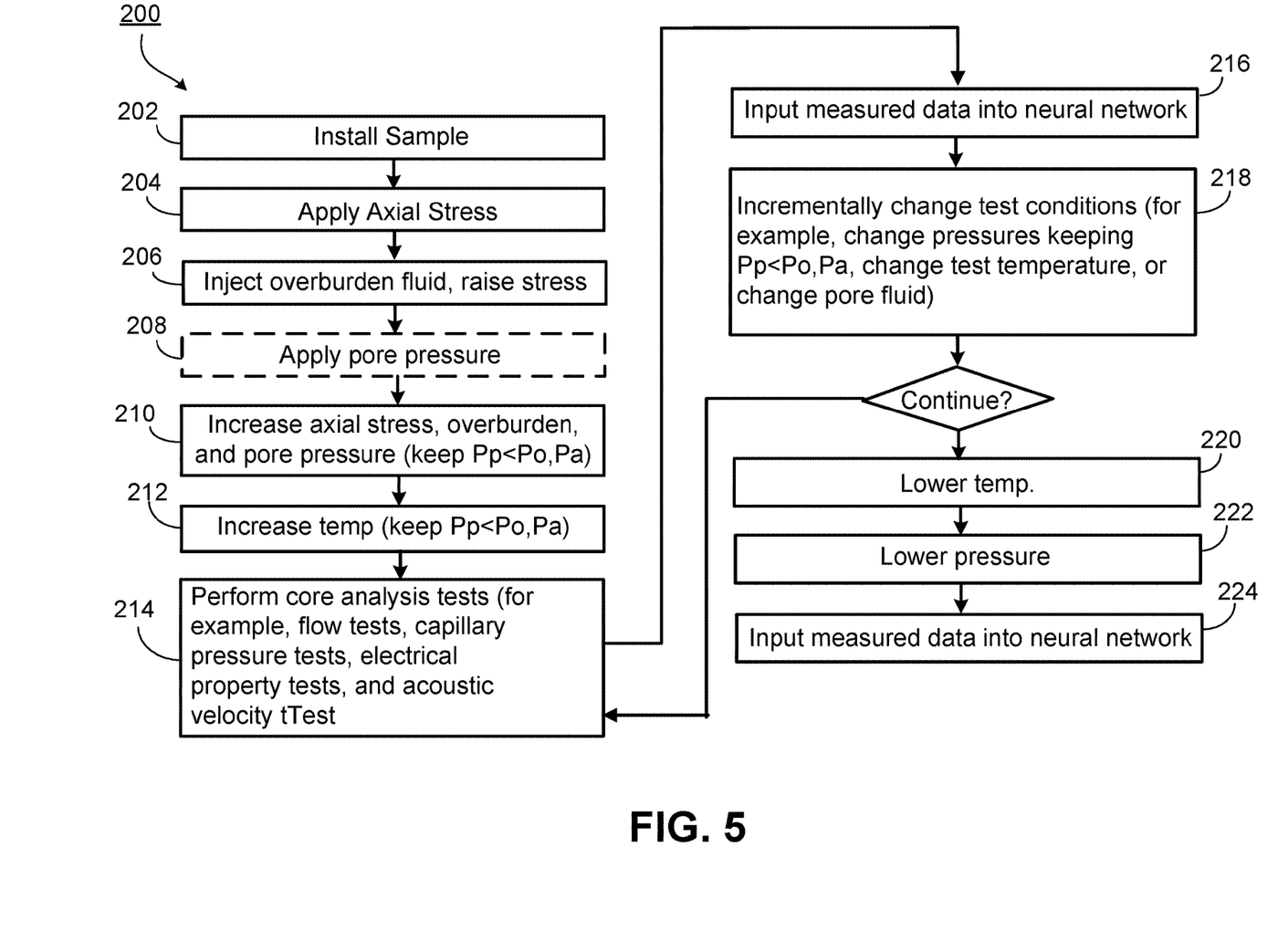
FIG. 5 is a flowchart of a method for performing a core analysis test.

FIG. 5 is a flowchart of a method 200 for performing a core analysis test with a sample at elevated pore fluid pressures. Core analysis tests include, for example, permeability, solvent cleaning, saturation, and capillary pressure tests. The method 200 can be executed using the test cell 134 shown in FIG. 2 with the centrifuge apparatus 102 shown in FIG. 1. To use the system 100, the sample 150 is installed in the test cell 134 (step 202). The installation starts with placing the sample 150 in the electrical measurement jacket 154. The body 144 of the test cell is placed on the base 140 and bolted into place. The sample 150 and the electrical measurement jacket 154 are then fixed on the end piece of the base 140. When the jacket 154 with the sample 150 is installed on 140, the O-rings 163 provide a seal so when confining fluid is injected, the jacket 154 is pressed against the base 140 and the seal 161. This creates a seal restricting confining fluid from entering the sample 150 within the jacket 154. The end cap 142 is installed on top of the body 144 and bolted into place forming the cell chamber 176 with the sample 150 and the electrical measurement jacket 154 inside. The test cell 134 is then placed in the centrifuge apparatus.

An axial stress (also referred to as axial pressure) is applied to the sample using the piston assembly 152 (step 204). The axial stress is determined by the fluid pressure applied to the piston fluid chamber 158 through the valve $194_5$. For example, an axial stress of 200 psi can be applied. Acoustic, electrical, and x-ray data gathered from the acoustic sensors 148, the electrical sensors 146, and the x-ray camera 132 are fed to the neural network 115. The neural network 115 evaluates the sample 150 using the procedures described in U.S. patent application Ser. No. 16/131,341 and the sample is replaced if necessary. For example, the neural network can receive electrical data and can verify that the electrical data is within an appropriate range (for example, a brine-saturated sample of specific pore structure will have a different signal than an oil saturated sample). Similarly, the acoustic (sonic) sensor signal is based on sample internal structure and fluid in it and the neural network can verify that the acoustic data is within an appropriate range. The x-ray data will also provide indications of any physical change such as cracks creating within the sample. The neural network will evaluate these data against a trained model and establish sample integrity If the sample 150 is acceptable, an overburden stress (also referred to as overburden pressure) is applied to the sample 150 (step 206). The centrifuge system fills the test cell 134 with overburden fluid through valve $194_2$ and bleeds air out of the cell chamber 176 through valve $194_3$ before applying the overburden stress at level below that of the axial stress. For example, an overburden stress of 150 psi can be applied. The overburden fluid in the cell chamber 176 is fluidly isolated and sealed from the sample 150 by the base 140, the piston assembly 152, the electrical measurement jacket 154, the piston seal 161, and the base seal 163. Acoustic, electrical, and x-ray data gathered from the acoustic sensors 148, the electrical sensors 146, and the x-ray camera 132 are fed to the neural network 115. The neural network 115 evaluates the sample 150 and the sample is replaced if necessary.

Optionally, a pore pressure can be applied to the sample 150 at level less than the level of the overburden stress (step 208). The pore pressure can be applied to the sample 150 through the valve $194_1$ and the valve $194_4$. For example, a pore pressure of 50 psi can be applied to the sample 150. Acoustic, electrical, and x-ray data gathered from the acoustic sensors 148, the electrical sensors 146, and the x-ray camera 132 are fed to the neural network 115. The neural network 115 evaluates the sample 150 and the sample is replaced if necessary.

After these initial conditions are established, the axial, overburden, and pore pressures are increased to test pressure conditions while keeping the pore pressure less than the overburden pressure and the overburden pressure less than the axial pressure (step 210). This pressure relationship is important If the overburden pressure gets higher than axial piston pressure, it will cause axial piston to retract into piston chamber creating a gap between sample 150 and piston 162. This will cause jacket 154 to fail and overburden oil to invade sample 150, so axial pressure must be higher than overburden. If pore pressure increase higher than overburden stress, it will cause jacket 154 to expand and seal 161 & 163 to fail causing pore fluid to leak in to the cell assembly and mix with overburden fluid, causing test failure.) Acoustic, electrical, and x-ray data gathered from the acoustic sensors 148, the electrical sensors 146, and the x-ray camera 132 are fed to the neural network 115. The neural network 115 evaluates the sample 150 and the sample is replaced if necessary.

After achieving test pressure conditions are achieved, the temperature in the test cell 134 is raised to the test temperature while keeping the pore pressure less than the overburden pressure and the overburden pressure less than the axial pressure (step 212). Acoustic, electrical, and x-ray data gathered from the acoustic sensors 148, the electrical sensors 146, and the x-ray camera 132 are fed to the neural network 115. The neural network 115 evaluates the sample 150 and the sample is replaced if necessary.

After test pressure and temperature conditions are established, one or more core analysis tests (for example, flow tests, capillary pressure tests, electrical property tests, and acoustic velocity tests) is performed (step 214). The pore pressure in the sample 150 can be controlled by the pressure of fluids in the first reservoir 182 and the second reservoir 184. The two-reservoir approach allows independent control of the pore pressure based at least in part on the pressure of test fluids in the first reservoir 182 and the second reservoir 184. The two-reservoir approach also allows the application of two different test fluids to the sample 150 and the application of one test fluid from one reservoir while fluids flushed from the sample 150 are collected in the other reservoir.

The location of the two reservoirs 182, 184 inside the pressure boundary of the test cell keeps the two reservoir 182, 184 under pressure, this enables the fluids 183, 185 to be two different fluids with dissolved gas at pressure and temperature. For example, one fluid could be formation water with dissolved gas and the other fluid could be formation oil with dissolved gas. The dissolved gas remains soluble in the liquid phase only due to the elevated pressure. The two fluids could be both liquid, both gas, or one liquid and one gas.

During and after the test(s) being performed, acoustic, electrical, and x-ray data gathered from the acoustic sensors 148, the electrical sensors 146, and the x-ray camera 132 are fed to the neural network 115 (step 216). The neural network 115 evaluates the sample 150 and the sample is replaced if necessary.

If the sample is still intact, other tests can be performed or same test can be performed under different conditions. For example, the pressure conditions can be changed, the temperature can be changed, the pore fluid can be changed, or a combination of these changes can be applied (step 218).

After testing is completed, the centrifuge apparatus 102 is returned to a state in which the user can remove the sample 150 and add a new sample. The centrifuge apparatus 102 lowers the temperature of the sample to ambient conditions while keeping the pore pressure less than the overburden pressure and the overburden pressure less than the axial pressure (step 220). Acoustic, electrical, and x-ray data gathered from the acoustic sensors 148, the electrical sensors 146, and the x-ray camera 132 are fed to the neural network 115. The pore pressure, axial pressure, and overburden pressure are lowered to atmospheric conditions while keeping the pore pressure less than the overburden pressure and the overburden pressure less than the axial pressure until each of the pressures sequentially reaches atmospheric conditions (step 222). Acoustic, electrical, and x-ray data gathered from the acoustic sensors 148, the electrical sensors 146, and the x-ray camera 132 are fed to the neural network 115 (step 224).

The method 200 is described as being implemented in conjunction with a computer system 103 implementing a neural network 115. Although data communication and sample condition assessment is described as being performed after each step, this is optional. Some methods are implemented with less frequent data communication and sample condition assessment. In addition, the method 200 can also be performed in conjunction with a conventional control and data gathering computer system that does not include a neural network. Without a neural network, the automated monitoring and assessment of sample condition must be performed manually.

Figure 6:
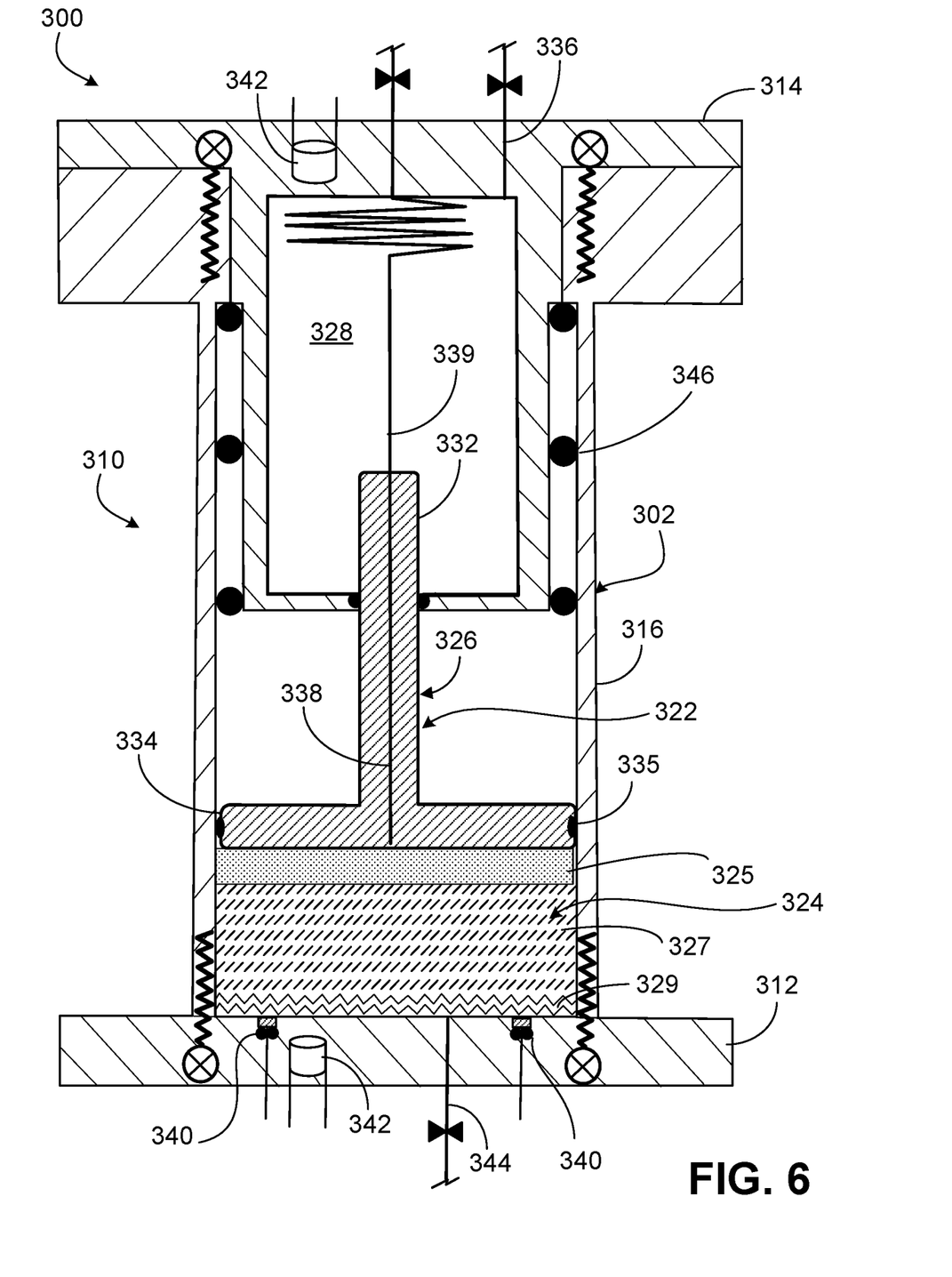
FIG. 6 is a schematic cross-sectional view of a test cell.

FIG. 6 shows a test cell 300 that can be used to test phase behavior of a sample. In contrast to some test cells, the test cell 300 can be centrifuged which enables separation of suspended particles (wax, asphaltene, precipitates etc.) that cannot be achieved without centrifugation of the pressurize cell. The test cell 300 can also be used to quantify particles that are created at each step of tests (without centrifugation the particles cannot be quantified as they remain either suspended or stick to cell internal body). After using a centrifuge to separate these particles based on their densities, the particles can be quantified with acoustic and x-ray analysis. The X-ray and acoustic analysis can also help provide size of these particles. The test cell 300 can also be used to segregate fluids based on density variations. In particular, the test cell 300 can also be used to separate of gas from other fluids and establish of clear fluid boundaries to quantify various fluids. The test cell 300 can measure changes in electrical properties that help in understanding fluid and particle properties.

The test cell 300 includes a casing 310 that includes first end piece (a base 312), a second end piece (an end cap 314), a body 316 extending between the base 312 and the end cap 314, at least one electrical sensor 318, at least one acoustic sensor 320, and a piston assembly 322. The body 316 is a generally cylindrical member with an inner bore. The base 312 and the end cap 314 are bolted to the body 316 of the casing 310. The casing 310 can be made of material such as, for example, titanium, Torlon®, glass. Although not shown in FIG. 6, the test cell 300 includes processing units similar to those described with respect to the test cell 134.

In contrast to the test cell 134, the test cell 300 does not include a discrete sample holder. Rather, the test cell 300 holds samples in a sample chamber 324 defined between the base 312, the body 316, and the piston assembly 322. In general, materials for the piston assembly 322 and the base 312 should be penetrable to x-rays and have minimal or no electrical conductance and can be, for example, Torlon® (available from Solvay Plastics) or glass. Base 312 is flat to avoid non-uniform collection of solid particles during the test. The test cell 300 is illustrated with a first sample 325, a second sample 327, and a third sample 329 in the sample chamber 324. During typical phase behavior testing, the first sample 325 can be a solid or a fluid, the second sample 327 is a fluid, and the third sample 329 can be a solid or a fluid.

Piston assembly 322 includes a piston member 326, and a piston fluid chamber 328. An axial pressure fluid supply line 330 supplies fluid to piston fluid chamber 328. The piston member 326 has a stem 332 and a head 334. A piston fluid chamber base has an opening through which the stem 332 of piston member 326 extends. An end face of piston member 326 defines one end of the sample chamber 324.

The first sample 325, the second sample 327, and the third sample 329 are contained between the end face of the piston member 326 and the end face of base 312. As fluid is added to the piston fluid chamber 328 by way of axial pressure fluid supply line 336, the end face of piston member 156 applies axial force to the first sample 325, inducing axial stress in the samples. The end face of piston member 326 and the end face of the base 312 can be coated with a substance, such as Teflon®, that will provide electrical isolation of the samples. A seal 335 is disposed between the piston head 334 and the wall 319 to limit or prevent fluid from flowing between the piston head 334 and the body 316.

The stem 332 of the piston member 326 defines an inner channel 338 that extends to the sample chamber 324. The inner channel 338 is attached to a conduit 339 that extends from the stem 332 through the piston fluid chamber 328 and the end cap 314. The conduit 339 is made of a flexible material to compensate for movement of the piston member 326 during testing. Test fluid can be supplied to the sample chamber 324 or fluid can be withdrawn from the sample chamber 324 through the inner channel 338 and the conduit 339.

The test cell 300 further includes two electrical probes 340 in the base 312 of the casing 310 and two acoustic sensors 342 (one in the base 312 and one in the end cap 314). The electrical probes 340 and the acoustic sensors 342 can be generally similar to the electrical probes and the acoustic sensors described with respect to the test cell 134. The electrical probes 340 measure electrical properties of the first sample 325, the second sample 327, and the third sample 329 and the acoustic sensors 342 measure acoustic properties of the first sample 325, the second sample 327, and the third sample 329. The x-ray device 106 in the centrifuge apparatus 102 images the first sample 325, the second sample 327, and the third sample 329.

A test fluid line 344 extends through the base 312. Test fluid can be supplied to the sample chamber 324 or fluid can be withdrawn from the sample chamber 324 through the test fluid line 344.

Three seals 346 are disposed between the end cap 314 and the body 316 to limit or prevent fluid from flowing between the end cap 314 and the body 316. The three seals provide an additional safety in dealing with fluids that can have high gas content and corrosive components that can damage O-rings (seal). If one of the seal (O-rings) is compromised, there will be indications both in pressure variation and x-ray observations. While the other seals are holding, the test process can be safely stopped.

The test cell 300 can used to perform the experimental studies including: saturation pressure test for bubble and due point, utilizing centrifugal force to separate various fluids quickly and utilizing x-ray to identify phase boundary and volume of each fluid; coefficient of compressibility on the reservoir fluids as a function of temperature and composition; pressure volume relationship of reservoir fluids as function of temperature and composition; differential gas liberation test along with compressibility of each stage left over fluids; constant volume depletion test; recombination of fluid for EOR studies for miscible and immiscible fluids; fluid-fluid compatibility for injected & produced fluids with reservoir fluids; wax appearance temperature prediction and quantifying amount of wax; asphaltene prediction and quantification and sizing of asphaltene, both in suspended phase and precipitated phase; determination of asphaltene offset pressure, asphaltene conglomeration pressure and asphaltene precipitation pressure; understanding effect of asphaltene on acoustic velocity and electrical properties measurements with utilization brine saturated core disk; understanding wettability change due to compositional change of reservoir hydrocarbon fluid as function of pressure drop; study crystallization of salt as function of temperature and pressure; study hydrates formation and dissociation as function of temperature, pressure, gas composition and brine salinity. Understanding of onset, size, quantity and type of hydrates; study of emulsion formation, quantity and size as function of temperature, pressure and composition; and condensate anti-banking treatment study.

Figure 7:
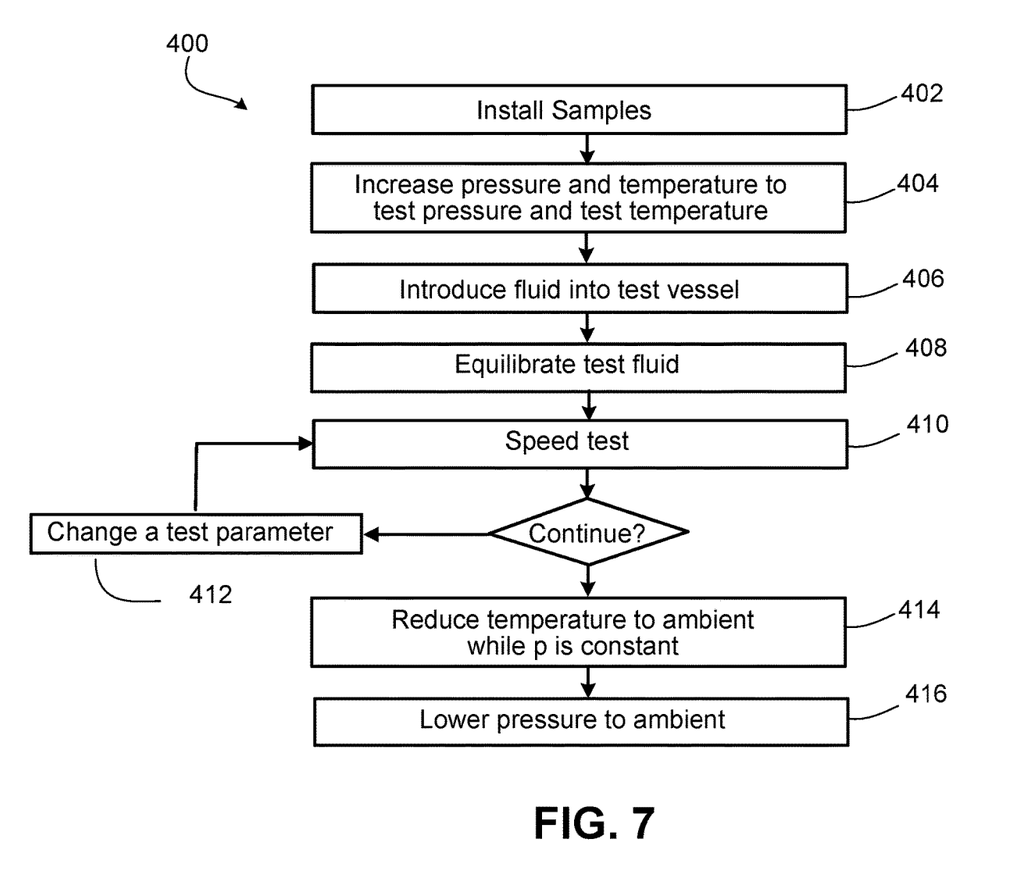
FIG. 7 is a flowchart of a method for performing a phase behavior test.

FIG. 7 is a flowchart of a method 400 for performing phase behavior tests. The method 400 can be performed using the centrifuge apparatus 102, shown in FIG. 1, and the test cell 300, shown in FIG. 6. The first sample 325, the second sample 327, and the third sample 329 are installed into the test cell 300 (step 402). The body 316 of the test cell 300 is bolted into place on the base 312. The third sample 329 is placed in the body 316, followed by the second sample 327 and then the first sample 325. The end cap 314 with the piston assembly 322 is placed on the body 316 and bolted into place.

In some cases, the test is performed on a sample consisting of a single fluid (for example, a gas-saturated fluid). In this approach, the piston 226 is in contact with the base 312 and the complete cell 300 is assembled. After the cell 300 is assembled, the chamber 328 is filled through the line 336 and pressurized to the pressure of the test fluid. An inert fluid (typically a gas) is first injected in the test cell 300 through the line 336 to separate the piston slightly (~1 mm) from the base 312. The pressurized test fluid is then injected into the test cell 300 through the line 344 to load the required amount of the test fluid while moving piston 326 and maintaining pressure all time. Once the test fluid is loaded, the inert fluid is removed from the test cell 300 through the line 336. In some cases, the sample 329 is a solid sample. The solid sample 329 is first placed in the test cell 300 and the piston 326 is brought in contact with solid sample 329. The other test fluids are then loaded as explained with reference to testing a single fluid sample. After the test cell 300 is placed in one of the recesses 122 of the centrifuge apparatus 102, fluid is supplied to the piston fluid chamber 328 to move the piston head 334 to contact the first test sample 325.

The pressure and temperature of the test cell 300 are raised to test conditions (step 404). The pressure can be raised by injecting an inert fluid (for example, nitrogen) into the sample chamber 324 through the inner channel 338 and the conduit 339, the test fluid line 344, or both while increasing pressure in the piston fluid chamber 328.

A test fluid is then introduced into the test cell 300 (step 406). The test fluid can be introduced to the sample chamber 324 through the inner channel 338 and the conduit 339, the test fluid line 344, or both. Examples of test fluids include formation brine, oil, gas; condensate; chemicals for enhance oil recovery; fluid mixed with propant used for fracturing or other fluids that are produced or injected into the reservoir. Acoustic, electrical, and x-ray data gathered from the acoustic sensors 342, the electrical sensors 340, and the x-ray camera 132 are fed to the neural network 115. The neural network 115 evaluates the first sample 325, the second sample 327, and the third sample 329 and the samples are replaced if necessary. For example, the acoustic, electrical, and X-ray sensors provide information about the fluid phases in the test chamber to the neural network. If the received information does not match with the predetermined range that the neural network has been trained on, the sample can be replaced. For example, the density of the sample(s) could be calculated with information from the acoustic sensor; the resistivity/conductivity can be monitored with information from the electrical sensor; and phase separation or solid particles indicating failure of test fluid sample can be detected based on information from the x-ray sensor.

If the samples are acceptable, the test fluid is equilibrated for a desired time or parameter (step 408). After equilibration, acoustic, electrical, and x-ray data gathered from the acoustic sensors 342, the electrical sensors 340, and the x-ray camera 132 are fed to the neural network 115. The neural network 115 evaluates the first sample 325, the second sample 327, and the third sample 329 and the samples are replaced if necessary.

If the samples are still acceptable after equilibration, the system 100 performs a single-speed test, a multi-speed test, or both (step 410). Acoustic, electrical, and x-ray data gathered from the acoustic sensors 342, the electrical sensors 340, and the x-ray camera 132 are fed to the neural network 115. If additional testing is to be performed, at least test parameter is changed (step 412). Test parameters can be changed by, for example, changing test pressure, changing test temperature, withdrawing a fluid sample and perform compositional analysis, and modifying/changing the test fluid. Acoustic, electrical, and x-ray data gathered from the acoustic sensors 342, the electrical sensors 340, and the x-ray camera 132 are fed to the neural network 115. The neural network 115 evaluates the first sample 325, the second sample 327, and the third sample 329 and the samples are replaced if necessary.

After testing is complete, the system 100 transitions into a mode in which the test sample can be removed and a new sample can be added. The system temperature is lowered to ambient temperature while keeping the pressure constant (step 414). Acoustic, electrical, and x-ray data gathered from the acoustic sensors 342, the electrical sensors 340, and the x-ray camera 132 are fed to the neural network 115. The pressure is then lowered to ambient (step 416). Acoustic, electrical, and x-ray data gathered from the acoustic sensors 342, the electrical sensors 340, and the x-ray camera 132 are fed to the neural network 115.

The method 700 is described as being implemented in conjunction with a computer system 103 implementing a neural network 115. Although data communication and sample condition assessment is described as being performed after each step, this is optional. Some methods are implemented with less frequent data communication and sample condition assessment. In addition, the method 200 can also be performed in conjunction with a conventional control and data gathering computer system that does not include a neural network. Without a neural network, the automated monitoring and assessment of sample condition must be performed manually.

Figure 8:
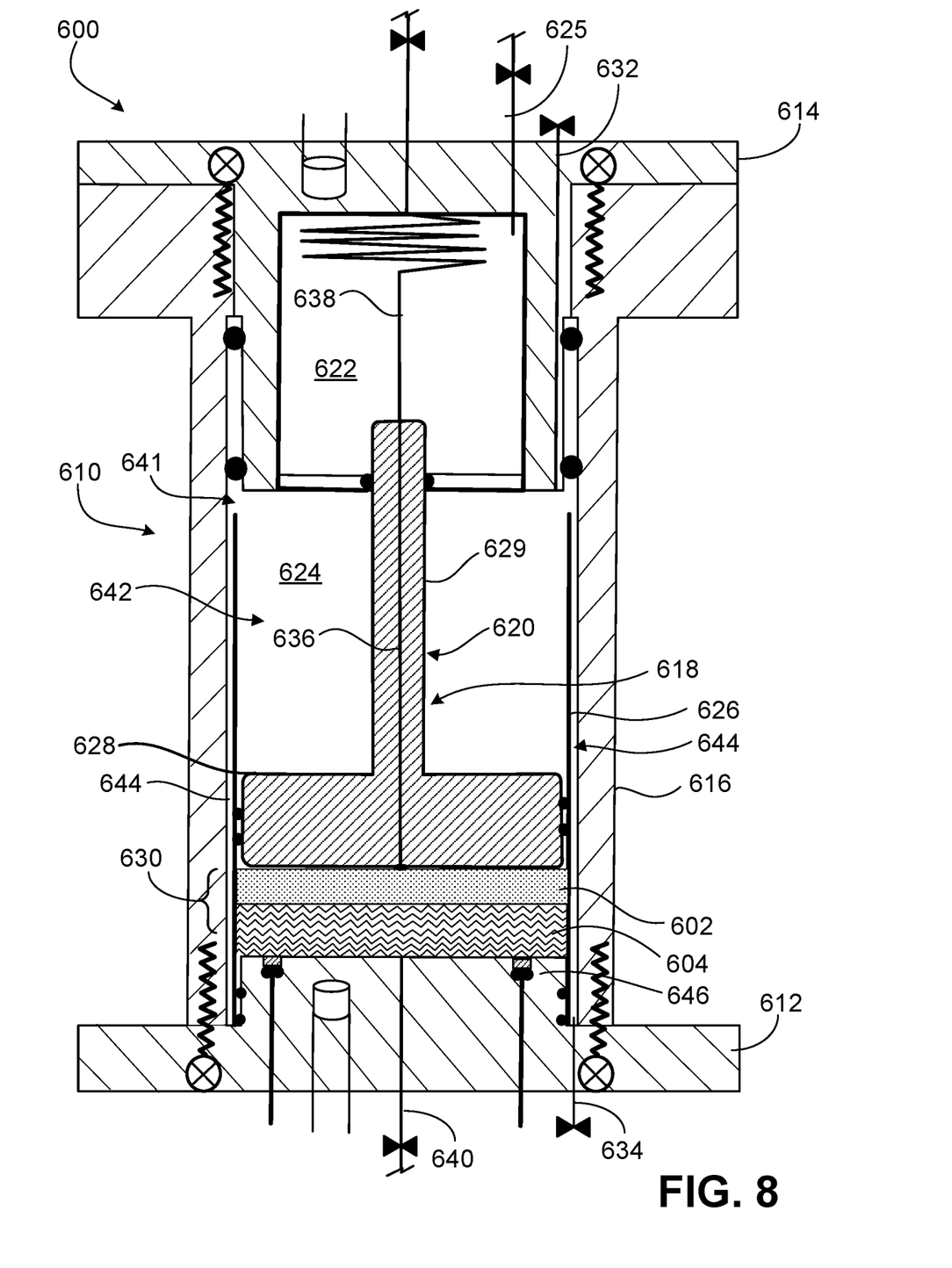
FIG. 8 is a schematic cross-sectional view of a test cell.

FIG. 8 shows a test cell 600 for testing cement setting, curing, and integrity using the centrifuge apparatus 102. Test cell 600 is structured similarly to test cell 300 but is used to test properties of samples that can change from fluid form to solid form during a test cycle.

The test cell 600 includes a housing 610 that includes a first end (base 612) and a second end (end cap 614). A body 616 extends from the base 612 to the end cap 614. In the housing 610, the base 612, the end cap 614, and the body 616 are three different components that are bolted together.

The test cell 600 also includes a piston assembly 618 with a piston 620 and a piston fluid chamber 622. The body 616, the base 612, and the end cap 614 define a piston chamber 624. A axial hydraulic fluid line 625 extends through the end cap 614 and can be used supply hydraulic fluid to and remove hydraulic fluid from the piston fluid chamber.

A rubber jacket 626 extends parallel to body 616 within the piston chamber 624. The piston 620 has a head 628 and a stem 629 and is movable within the piston chamber 624. The head 628 of the piston 620 is sized to move within the rubber jacket 626. O-rings between the rubber jacket 626 and the head 628 create a fluid seal to limit or prevent the movement of the test samples past the head 628. The head 628, rubber jacket 626, and the base 612 of the housing 610 define a sample chamber 630 within the piston chamber 624.

The test cell 600 includes a first overburden fluid line 632 defined extending through the base 612 to the piston chamber 624 and a second overburden fluid line 634 defined extending through the end cap 614 to the piston chamber 624. The stem 629 of the piston member 326 defines an inner channel 636 that extends to the sample chamber 630. The inner channel 636 is attached to a conduit 638 that extends from the stem 629 through the piston fluid chamber 622 and the end cap 614. The conduit 638 is made of a flexible material to compensate for movement of the piston 620 during testing. Test fluid can be supplied to the sample chamber 630 or fluid can be withdrawn from the sample chamber 630 through the inner channel 636 and the conduit 638. A test fluid line 640 extends through the base 612. Test fluid can be supplied to the sample chamber 630 or fluid can be withdrawn from the sample chamber 630 through the test fluid line 640.

In use, the head 628 contacts a water layer 602 and applies pressure on the water layer 602 (up to 50,000 psi). The water layer 602 and the cement slurry 604 undergo a phase change, from fluid to solid, while in the sample chamber 630. A pore pressure, generated by flowing a test fluid into the sample chamber 630 can be applied to the samples before, during, or after the phase change. [This approach can simulate fluid flow during the various stage of cement tests with established permeability as, there are formation fluid that may invade cement during setting and curing. This approach also simulates the effect of fluid flow on quality of final set cement including the effect of reaction(s) between cement components and the fluid to help evaluate and improve cements and design better ones. The piston 620 is capable of moving at least three times the length of the test sample.

The rubber jacket 626 extends only partially up the body 616, from the base 612 towards the end cap 614. The rubber jacket 626 contacts the base 612 of the housing, but does not reach the end cap 614 of the housing 610. Rather the rubber jacket 626 is shorter than the body 616 to provide an opening 641 that facilitates fluid connection between a first space 642 in the piston chamber 624 and an outer channel 644 defined between the rubber jacket 626 and the body 616. The first space 642, like the sample chamber 630, is partially defined by the head 628 and the rubber jacket 626. The first space 642, however, is defined by the opposite side of the head 628 relative to the sample chamber 630. The piston chamber 624 therefore includes the sample chamber 630, the first space 642, and the outer channel 644. The head 628 and stem 524, extend into the piston chamber 624 to apply mechanical pressure and a test fluid (pore) pressure to the cement slurry and associated water layer.

The movement of the head 628 changes the volumes of the first space 642 and sample chamber 630. For example, as the head 628 moves towards the water 602, the volume of the first space 642 increases while the volume of the sample chamber 630 decreases. The volume of the outer channel 644 remains constant regardless of the position of the piston 620 because, unlike the first space 642 and the sample chamber 630, the outer channel 644 is not defined by the piston 620. The outer channel 644 facilitates the flow of a confining fluid that fills the first space 642.

The test cell 300 can used to perform the experimental studies including: cement thickening time test under true tri-axial condition with pore pressure with or without reservoir rock & casing; cement setting and curing time and record of dynamic changes before, during and after curing/setting; measurement of free water before and after cement is set to evaluate cement hydration & seal capacity; fluid injection to evaluate permeability of cement matrix; fluid flow to measure seal strength and effectiveness between cerement and reservoir rock and casing material; measurement of solid/liquid/gas additive dispersion during setting and curing of cement; hydrostatic compressive strength test on set cement and leakage/seal capacity during various stage before failure and after failure; tri-axial compressive strength test on set cement and leakage/seal capacity during various stage before failure and after failure; Poison ratio and Young modulus of cement both static and dynamic; effect of drilling fluid on bonding capacity of cement to reservoir rock and casing; effect of acidizing and fracturing fluid on cement; study of gas migration; and measurement of electrical property and sonic velocity for calibrating bond logs.

Figure 9:
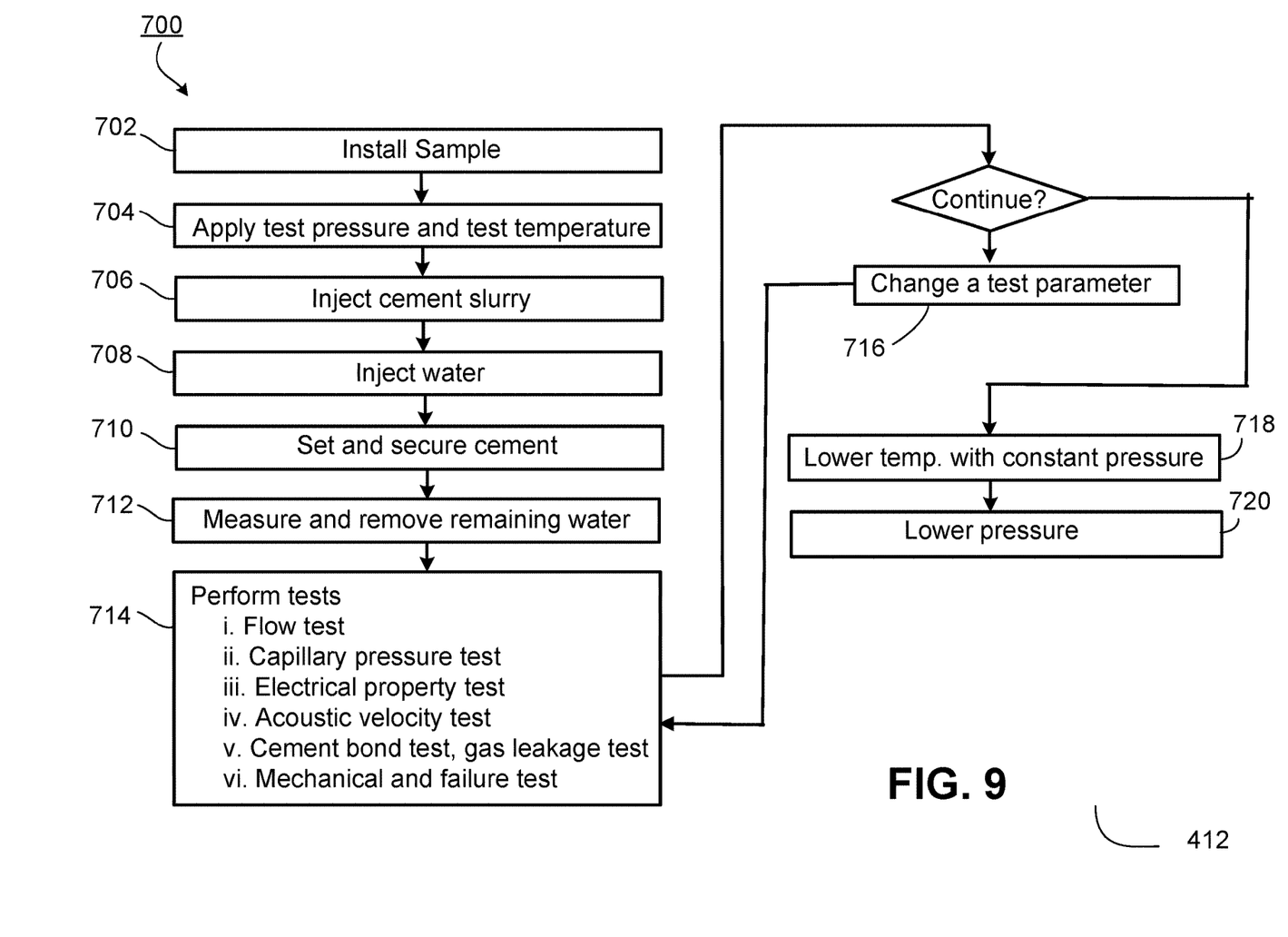
FIG. 9 is a flowchart of a method for performing a cement test.

FIG. 9 is a flowchart for a method 700 for performing setting, curing, and integrity tests. The method 700 can be performed using test cell 600, shown in FIG. 8, and the centrifuge apparatus 102, shown in FIG. 1.

The test cell 600 is assembled by bolting body 616 onto the base 612 and bolting the end cap 614 onto the body 616 with the rubber jacket 626 in position. If a hollow reservoir rock is being included, the hollow reservoir rock is installed in the sample chamber 630 during the assembly process (step 702). Fluid is supplied to the piston fluid chamber 622 through the axial hydraulic fluid line 625 to extend the piston 620 and place the head 628 of the piston 620 in contact with the base 612 or the hollow reservoir rock if present. The piston chamber 624 is filled with overburden fluid through the second overburden fluid line 634 while air bleeds out through the first overburden fluid line 632. After these initial conditions are established, the pressure and temperature in the test cell 600 are raised to test conditions (step 704).

A cement slurry being tested is injected into the sample chamber 630 through the test fluid line 640 (step 706). While the cement slurry is being injected, hydraulic fluid is being released from the piston fluid chamber 622 through the axial hydraulic fluid line 625 and overburden fluid is being released from the piston chamber 624 through the first overburden fluid line 632. Acoustic, electrical, and x-ray data gathered from the acoustic sensors 342, the electrical sensors 340, and the x-ray camera 132 are fed to the neural network 115. The neural network 115 evaluates the sample and the sample is replaced if necessary. For example, acoustic, x-ray, and electrical sensors data is fed to the trained neural network to confirm cement components are not separating and that particles, fluids and gas are uniformly distributed. For example, in case of cement with fiber, beads or gas (foam cement), it is important that dispersion is uniform during loading slurry, curing and setting of cement.

The system 100 then injects water into the sample chamber 630 until a desired volume of free water 602 is present on top of the slurry 604 (step 708). Acoustic, electrical, and x-ray data gathered from the acoustic sensors 342, the electrical sensors 340, and the x-ray camera 132 are fed to the neural network 115. The neural network 115 evaluates the sample and the sample is replaced if necessary.

The cement slurry 604 sets and cures (step 710). During this process, the cement slurry imbibes water from the free water layer 602. Depending on the test pressure and test temperature, the cement could set and cure for hours to weeks. [All the pressures (that is axial pressure, confining/overburden pressure, and pore pressure are applied and maintained during the loading of slurry, setting, curing and any tests during/after, curing/setting. Acoustic, electrical, and x-ray data gathered from the acoustic sensors 342, the electrical sensors 340, and the x-ray camera 132 are fed to the neural network 115 during the setting and curing process. After the setting and curing process is complete, Acoustic, electrical, and x-ray data gathered from the acoustic sensors 342, the electrical sensors 340, and the x-ray camera 132 are fed to the neural network 115. The neural network 115 evaluates the sample and the sample is replaced if necessary.

The remaining free water 602 is removed from the set and cured cement 604 and measured (step 712). Acoustic, electrical, and x-ray data gathered from the acoustic sensors 342, the electrical sensors 340, and the x-ray camera 132 are fed to the neural network 115 before testing is performed.

If the samples are still acceptable, the system 100 performs one or more tests associated with cement testing (step 714). Appropriate tests include, for example, flow tests, capillary pressure tests, electrical property tests, acoustic velocity tests, cement bond tests, gas leakage tests, mechanical tests, and failure tests. Acoustic, electrical, and x-ray data gathered from the acoustic sensors 342, the electrical sensors 340, and the x-ray camera 132 are fed to the neural network 115. If additional testing is to be performed, at least test parameter is changed (step 716). Test parameters can be changed by, for example, changing test pressure, changing test temperature, and modifying/changing the test fluid. Acoustic, electrical, and x-ray data gathered from the acoustic sensors 342, the electrical sensors 340, and the x-ray camera 132 are fed to the neural network 115. The neural network 115 evaluates the cement slurry 604 and the sample is replaced if necessary.

After testing is complete, the system 100 transitions into a mode in which the test sample can be removed and a new sample can be added. The system temperature is lowered to ambient temperature while keeping the pressure constant (step 718). Acoustic, electrical, and x-ray data gathered from the acoustic sensors 342, the electrical sensors 340, and the x-ray camera 132 are fed to the neural network 115. The pressure is then lowered to ambient (step 720). Acoustic, electrical, and x-ray data gathered from the acoustic sensors 342, the electrical sensors 340, and the x-ray camera 132 are fed to the neural network 115.

The method 700 is described as being implemented in conjunction with a computer system 103 implementing a neural network 115. Although data communication and sample condition assessment is described as being performed after each step, this is optional. Some methods are implemented with less frequent data communication and sample condition assessment. In addition, the method 700 can also be performed in conjunction with a conventional control and data gathering computer system that does not include a neural network. Without a neural network, the automated monitoring and assessment of sample condition must be performed manually.

A number of embodiments of the systems and methods have been described. Nevertheless, it will be understood that various modifications may be made without departing from the spirit and scope of this disclosure. Accordingly, other embodiments are within the scope of the following claims.

What is claimed is:

1. A system for testing properties of a sample, the system comprising:
    a test cell comprising:
        a cell casing comprising a first end piece, a second end piece, and a cylindrical body extending between the first end piece and the second end piece, the cell casing enclosing an interior region of the cell;
        a first reservoir;
        a second reservoir;
        a piston with a stem and a head, the head of the piston in sealing engagement with an inner surface of the cylindrical body of the test cell wherein the piston head and the first end piece at least partially define a sample chamber;
        an inner channel extending through the stem of the piston that extends to the sample chamber; and
        a sample line fluidly connected to the first reservoir and the sample chamber; and
        a circulation line attached to the inner channel that extends from the stem of the piston through the second end piece, wherein the circulation line fluidly connects to the second reservoir and the sample chamber.

2. The system of claim 1, wherein the piston is part of a piston assembly, the piston assembly also comprising a piston fluid chamber defined in the second end piece.

3. The system of claim 2, wherein the circulation line extends through the piston fluid chamber.

4. The system of claim 1, wherein the sample chamber is defined by the piston head, the first end piece, and the cylindrical body of the test cell.

5. The system of claim 1, wherein the sample chamber is defined by the piston head, the first end piece, and a cylindrical jacket parallel to the cylindrical body of the test cell, the cylindrical jacket extending between the piston head and the first end piece.

6. The system of claim 5, further comprising an overburden fluid supply line extending from a portion of the interior region outside the sample chamber through the cell casing.

7. The system of claim 1, wherein a surface of the first end piece exposed to the sample chamber is flat.

8. The system of claim 1, further comprising one or more processing units implementing a neural network.

9. The system of claim 8, further comprising an electrical probe incorporated in the first end piece adjacent the sample chamber, the electrical probe in communication with the neural network.

10. The system of claim 9, further comprising a first acoustic sensor incorporated in the second end piece, the first acoustic sensor in communication with the neural network.

11. The system of claim 10, further comprising a second acoustic sensor incorporated in the first end piece, the second acoustic sensor in communication with the neural network.

12. The system of claim 1, further comprising:
    a centrifuge with a plurality of recesses, each recess sized to receive the test cell.

13. The system of claim 12, wherein the centrifuge is part of a tri-axial centrifuge apparatus.

* * * * *